United States Patent

Bataillard et al.

[11] Patent Number: 5,482,372
[45] Date of Patent: Jan. 9, 1996

[54] FLOW CELL FOR CALORIMETRIC MEASUREMENTS

[75] Inventors: Pierre Bataillard, Kembs-Loechle, France; Alfredo E. Bruno, Oberwil, Switzerland

[73] Assignee: Ciba-Geigy Corporation, Tarrytown, N.Y.

[21] Appl. No.: 212,668

[22] Filed: Mar. 11, 1994

[30] Foreign Application Priority Data

Mar. 17, 1993 [EP] European Pat. Off. .............. 93810192

[51] Int. Cl.⁶ .......................... G01K 17/00; G01N 25/20
[52] U.S. Cl. ..................... 374/31; 374/148; 436/147; 422/51
[58] Field of Search ..................... 374/29, 31, 32, 374/147, 148; 436/147; 422/51; 73/204.11, 204.21

[56] References Cited

U.S. PATENT DOCUMENTS

| | | | |
|---|---|---|---|
| 3,552,207 | 1/1971 | Monk et al. | 436/147 |
| 3,665,762 | 5/1972 | Domen | 374/31 |
| 3,726,644 | 4/1973 | Desnoyers et al. | 436/147 |
| 3,740,194 | 6/1973 | Hendy | 374/31 |
| 3,834,873 | 9/1974 | Picker | 374/31 |
| 4,229,105 | 10/1980 | Silverbage | 356/246 |
| 4,869,597 | 9/1989 | Christopher | 374/37 |
| 4,892,707 | 1/1990 | Stockton et al. | 422/51 |
| 4,935,345 | 6/1990 | Guibean et al. | 435/14 |
| 4,993,842 | 2/1991 | Morimoto et al. | 374/29 |
| 5,083,145 | 1/1992 | Gundlach et al. | 346/159 |
| 5,167,450 | 12/1992 | Nukui et al. | 374/31 |

FOREIGN PATENT DOCUMENTS

| | | | |
|---|---|---|---|
| 2310565 | 5/1975 | France . | |
| 1333402 | 8/1987 | U.S.S.R. | 422/51 |

OTHER PUBLICATIONS

S. Sandarusi et al. Review of Scientific Instruments vol. 63, No. 2, Feb. 1992 pp. 1810–1821.

Primary Examiner—Thomas B. Will
Assistant Examiner—Andrew Hirshfeld
Attorney, Agent, or Firm—George R. Dohmann

[57] ABSTRACT

A flow cell for calorimetric measurements comprises a body (2) with at least one flow channel (3), which extends between an inlet opening (4) and an outlet opening (5), and a thermoelectric detector (16) for monitoring temperature changes, which occur during chemical or biochemical processes in a measuring volume (17). The measuring volume (17) is arranged in close vicinity of the outlet opening (5). The body (2) of the flow cell (1) has a good thermal conductivity of a magnitude such, that a fluid flowing through the flow channel (3) is thermostatizised prior to entering the measuring volume (17) solely by flowing through the flow channel (3) and free of any external thermostatization means. Thus, a flow cell is provided, which is capable of self-thermostatizing a fluid flowing therethrough.

19 Claims, 4 Drawing Sheets

FLOW CELL FOR CALORIMETRIC MEASUREMENTS

The invention relates to a flow cell for calorimetric measurements.

BACKGROUND OF THE INVENTION

In Chemistry the recording of thermal events is a well known and established technique and calorimetric measurements for the detection of the heat of chemical or biochemical reactions have become a technique of increasing importance. It opens a very broad range of applications both for analytical purposes in fields, such as, for example, clinical, environmental and bioprocess monitoring, and for the biological study of living cells and organisms. Traditional calorimeters, which are used for such calorimetric measurements, were developed some 30 years ago. They rely on very well isolated vessels and accurate temperature regulation thanks to voluminous thermostatted baths and heat exchanger coils. Since that time, there has been a progressive appearance of new, less tedious and time consuming calorimetric measuring methods, which are based on smaller, sometimes miniaturized devices dedicated for flow-through systems and allowing a continuous and automated monitoring of various processes. Regarding the thermal detection of chemical and biochemical processes two principal approaches can be distinguished, which strongly affect the instrumentation involved.

The first approach uses calorimeters, which are based on the quasi-adiabaticity of the thermal process. In these calorimeters heat exchanges between the vessel, usually a Dewar vessel, where the reaction takes place, and the external environment must be minimized. From this demand there results the need for vessels with a large internal volume of 10 cm$^3$ and more, for an excellent thermal insulation, for a differential arrangement and/or for an accurate compensation of the heat losses with these calorimeters. Such, an estimated amount of about 50% to 80% of the heat, which is produced in the examined chemical or biochemical process, contributes to the detected and recorded temperature change $\Delta T$.

From the prior art there are known so-called "enthalpimetric flow reactors", which work according to this first principle approach, and which are based on immobilized enzymes or microorganisms. In these devices the reaction vessel is replaced by a reactor column, that is packed with matrix-bound enzyme on a carrier substrate, where the chemical or biochemical reaction takes place. Although offering excellent performances, such as, for example, a temperature resolution of about $10^{-5}$K, these devices suffer from several disadvantages. As the devices are based on adiabaticity they need a sophisticated insulation, which makes the whole system complicated and voluminous. Thus the dimensions of such a device are about 50 cm×10 cm and its weight amounts to about 2 kg. In order to be able to perform the calorimetric measurements the device used must comprise at least two thermistors (temperature dependent resistors), which have to be very well matched. However, in practice, their common mode rejection ratio (CMRR), which is a measure for the accuracy of their matching, is limited to about 1000. That means that an apparent (false) $\Delta T$ of 0.001K will be observed if both thermistors are heated by 1K. Furthermore, the thermistors are part of a Wheatstone-Bridge circuitry and the necessary voltage applied to them may generate their self-heating, thus leading to artifacts. Lastly the devices suffer from the defficiencies of most devices employing columns, as these imply most of the time rather large dead volumes and hence, an increased analysis time. They are also liable to clog, especially when crude solutions from cultivation broths, or waste water samples, or samples with large molecules (e.g. cholesterol) rate to be analyzed.

The other approach is based on the principle of heat conduction. The heat, which is released during the chemical or biochemical process, is transfered from the reaction vessel to a surrounding heat sink. The heat flow between the reaction vessel and the heat sink is usually measured with a thermopile. A thermopile is a thermoelectric detector which works according to the principle of the Seebeck effect. The temperature difference across the thermocouples of the thermopile is proportionally related to a voltage between its cold and hot junctions. The sensitivities of thermopiles are typically expressed in V/W. Thus, the voltage output signal of the thermopile is proportional to the detected temperature change $\Delta T$. Such calorimeters, which are based on heat conduction, play an important role in investigations of living systems. Among these known calorimeters, which have special designs for a number of biological experiments, there are flow-through systems using flow cells, which allow the detection of released heat amounts down to some tenths of $\mu W$. However, these systems also need a complicated temperature control in form of a high mass of insulating material in order to achieve the required high temperature stability and inertia. Therefore these flow cells for calorimetric measurements are voluminous, costly and exhibit long equilibration times.

SUMMARY OF THE INVENTION

There is a need for an analytical calorimetric measurement device, more particularly for a flow cell for calorimetric measurements, which is based on the principle of heat conduction, and which is suited for a rapid, automated, and continuous analysis. The calorimetric measurement device shall avoid the defficiencies of the devices of the prior art and it shall allow enzymatic assays and drug screening using microorganisms. The calorimetric measurement device shall have only short equilibration and response times, and it shall thus display a dynamic behavior in terms of heat exchange. The objects of the present invention are therefore, to provide such a flow cell for calorimetric measurements which overcomes the defficiencies of the prior art devices, and which meets the above demands.

These objects are solved by a flow cell for calorimetric measurements which comprises a body with at least one channel, which extends between an inlet opening and an outlet opening, and a thermoelectric detector for monitoring temperature changes, which are released during chemical or biochemical processes in a measuring volume. The measuring volume is arranged in close vicinity of the outlet opening. The body of the flow cell has a good thermal conductivity of a magnitude such, that a fluid flowing through the channel is thermostatizised prior to entering the measuring chamber solely by flowing through the channel and free of any external thermostatization means. Thus, a flow cell is provided, which is capable of self-thermostatizing a fluid flowing therethrough. Preferrend embodiments of the invention comprise in addition the features of one or more of the dependent claims.

BRIEF DESCRIPTION OF THE DRAWINGS

Further objects of the invention will become apparent from the subsequent description of embodiments of the invention with reference to the accompanying schematic drawings in which.

DETAILED DESCRIPTION OF PREFERRED EMBODIMENTS

Figure 1:
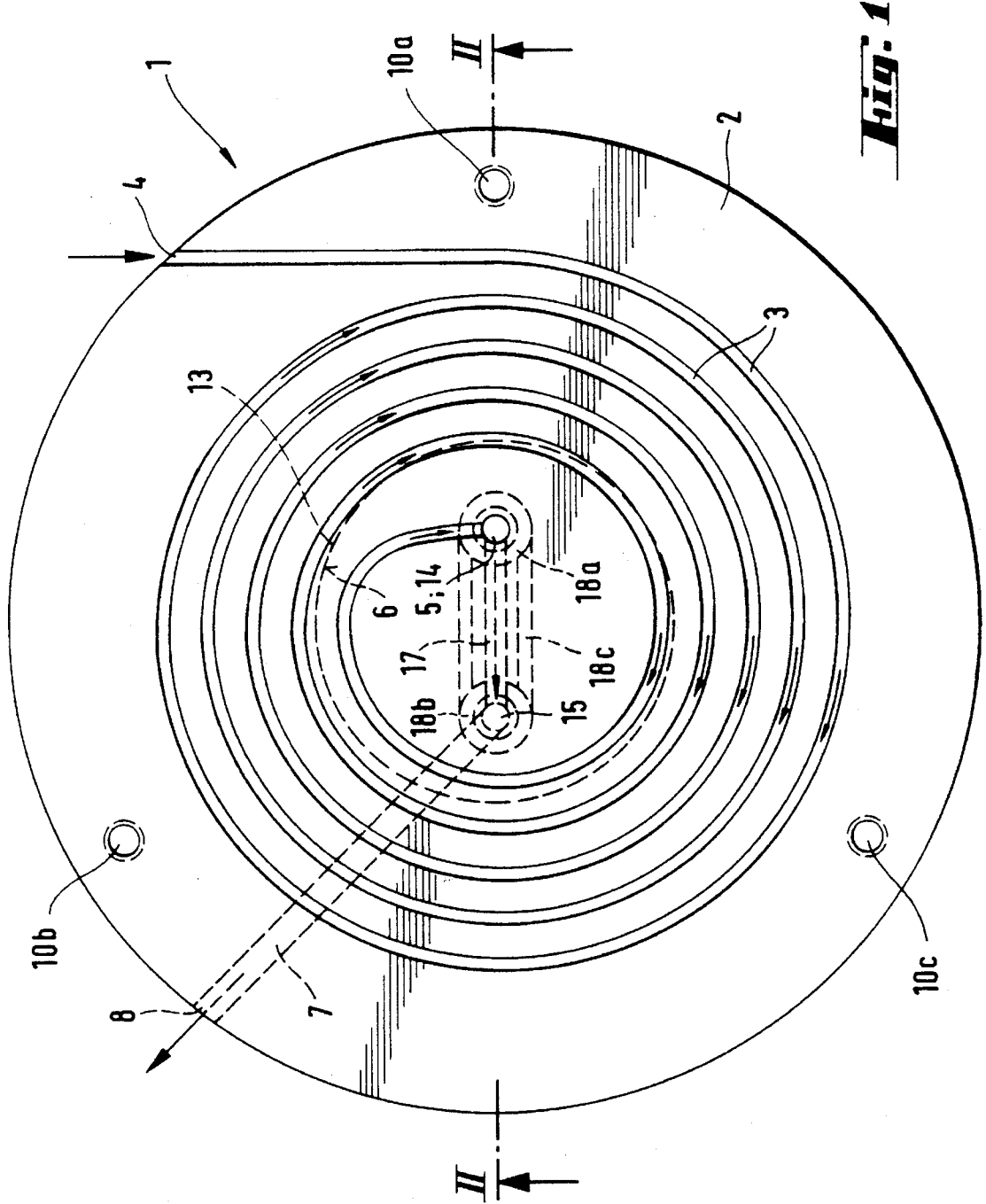
FIG. 1 is a top view of a first embodiment of the body of the flow cell according to the invention.
Figure 2:
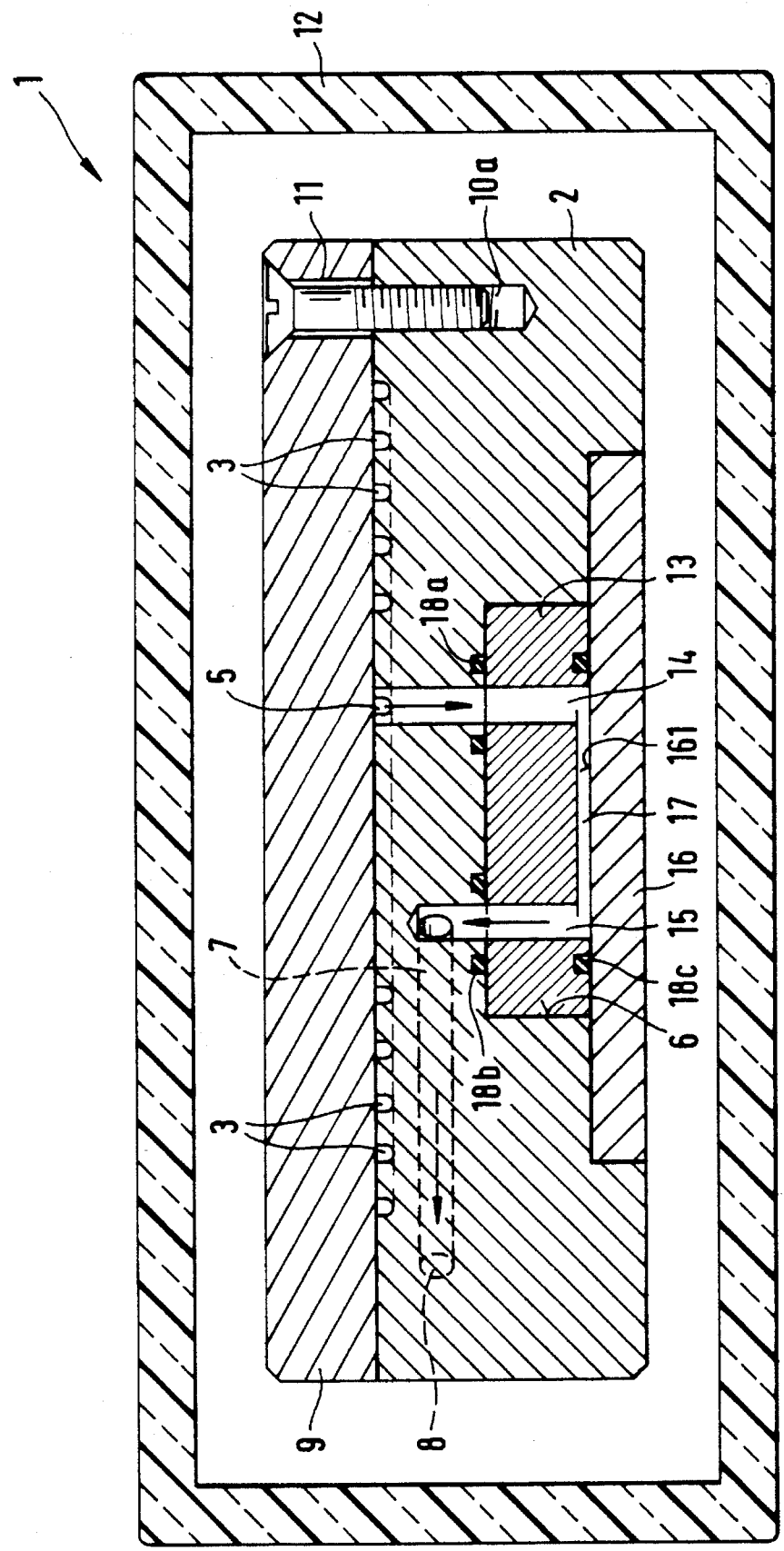
FIG. 2 is a sectioned view of the first embodiment of the flow cell as a whole along section line II—II in FIG. 1 (with its outer jacket)

A first embodiment of a flow cell for calorimetric measurements according to the invention is depicted in FIGS. 1 and 2 and generally designated with the reference numeral 1. It comprises a body 2 with at least one channel 3, which extends between an inlet opening 4 and an outlet opening 5. The body 2 is provided with a recess 6, which is located immediately adjacent to the outlet opening 5 and communicates with the channel 3. The recess 6 is designed to accomodate a thermoelectric detector 16 for monitoring amounts of heat, which are released during chemical or biochemical processes in a measuring volume 17. The measuring volume 17 is defined by a small gap which is formed between the active surface 161 of the detector 16 and a spacer element 13. The spacer element 13 is arranged in the recess 6 beween the detector 16 and the outlet opening 5 and has two vertical bores 14 and 15. The first bore 14 communicates with the outlet opening 5 of the channel 3, while the second bore 15 leads into an exit channel 7 which extends about laterally through the body 2 and ends at an exit opening 8, preferably at the periphery of the body 2. Sealings 18a and 18b are provided around the bores 14, 15 between the spacer element 13 and the body 2. A further sealing element 18c is provided between the spacer element 13 and the detector 16. The sealings 18a–c allow a fluid-tight flow from the channel 3, through the outlet opening 5 into the bore 14, across the active surface 161 of the thermoelectric detector 16 to the bore 15, and from there through the exit channel 7 to the exit opening 8 at the periphery of the body 2.

By inserting spacer elements 13 of varying heights the width of the gap between the active surface 161 of the thermoelectric detector 16 and the spacer element 13 and thus the measuring volume 17 can be modified. As shown in the Figures the height of the central part of the spacer element 13 can be smaller than on the periphery, thus forming a wider gap and a greater measuring volume 17. The central part can also protrude towards the thermoelectric detector 16, thus resulting in a very small measuring volume. The measuring volumes are preferably adjustable from about 10 µl to about 100 µl.

The thermoelectric detector is preferably a thermopile, such as the ones available from "Xensor Integration, Delft, The Netherlands. The active surface 161 of the thermopile 16 can be covered with a reactive substance, which is chosen according to the analysis that shall be accomplished. Thus, the reactive substance can be, for example, an enzyme which is immobilized within a cavity in the thermopile. Upon passing through the measuring volume 17 the fluid reacts with the substance on the reactive surface of the thermopile and a temperature change occurs which is detected by the thermopile. The signals which are produced by the thermopile are then recorded.

According to the first embodiment of the flow cell 1 the inlet opening 4 of the channel 3 is located at the periphery of the body 2, which has about the shape of a cylindrical slice piece. The outlet opening 5 of the channel 3 is located about in the central part of the body 2. The channel 3 extends generally about planar across the body 2 and has a curved shape, with a radius of curvature, that gradually decreases from the inlet opening 4 to the outlet opening 5 of the channel 3. Most preferably the channel 3 is spirally shaped. The outlet opening 5 of the channel 3 extends vertically through the body 2 and ends at the recess 6, which is arranged immediately adjacent to the outlet opening 5 and below the channel 3.

The body 2 of the flow cell 1 is made of a material which has a good thermal conductivity. Preferably the thermal conductivity of the body is better than about 0.801 W/cm-K in order to allow a quick heat exchange. Thus, by providing a flow cell for calorimetric measurements that has a body 2 of good thermal conductance, a fluid flowing through the channel is thermostatizised immediately prior to flowing past the thermoelectric detector 16 in the recess 6 solely by flowing through the channel 3, and free of any external thermostatization means. By having the inlet opening 4 at the periphery of the body 2 and the outlet opening 5 in the central part of the body 2 the calorimetric detection (through the thermopile) is carried out in that part of the flow cell, where there is achieved the highest temperature stability. Due to the spirally shaped flow channel 3, respective outer windings of the spiral thermally shield respective neighbouring inner ones. Because of the good thermal conductivity of the material of the body 3, a fluid, which enters the flow cell through the inlet opening 4 and might have temperature fluctuations along its volume elements, is thermally self-stabilized solely due to thermal equilibration during its movement through the flow channel 3. Therefore only a thermally stabilized fluid leaves the channel 3 through the outlet opening 5 of the channel 3. The material of the spacer 13 also has a good conductivity, which preferably corresponds to that of the body 2. Most preferably the spacer 13 is of the same material as the body 2. Such, the temperature of the fluid can be even further equilibrated from the outlet 5 of the channel 3 to the measuring volume 17 of the detector 16 and even the smallest thermal distortion of the fluid in that part of the flow cell is avoided. However, in comparison to the length of the flow channel 3, the height of the spacer element 13 usually is very small; therfore its influence on the thermal equilibration of the fluid can usually can be neglected.

The length of the flow channel 3 in conjunction with the pump rate of the fluid determines the residence time of the fluid in the channel 3 prior to reaching the thermoelectric detector 16. The residence time which is necessary to achieve a sufficient thermal equilibration is preferably chosen to be greater than about 0.5 seconds. A residence time shorter than 0.5 seconds leads to an insufficient thermal stabilization of the fluid and therefore results in high drifts of the detected signal. Moreover, fast flow rates of the fluid through the system result in over-pressure which can even destroy the thermopile. In flow injection analysis FIA a residence time longer than 300 seconds leads to a strong peak broadening due to the slow pumping rate. The analysis time becomes so long that it is not any longer compatible with a flowing method. Because of the low pumping rate the already optimized detection volume of the thermopile, which amounts to about 10 µl, is not filled within a reasonable time period and analysis cannot not be performed. However, in non-transient analytic methods employing very low pumping rates even residence times greater than 300 seconds are possible.

While for the body 2 of the flow cell 1 materials with a high specific heat capacity $C_p$ are desirable, it has been found that the physical mass of the body 2 (and of the spacer element 13, which for this limitation is considered a part of the body 2) of the flow-cell 1 has a strong influence on its performances. Therefore it is advantageous if the body 2 has a thermal mass, which is defined as the product of the specific heat capacity $C_p$ of the material of said body in J/g·K and of its physical mass in gramms, which amounts to less than about 50 J/K. Thus, the most preferred material for the body and the spacer of the flow cell is aluminium, as its rather high $C_p$ value is compensated by its density, which is the lowest of all the usual metals. Its thermal conductivity at the same time is one of the highest; only copper, gold and silver offer better values but they suffer on the other hand from high densities (Au), bad chemical stability and produce toxic salts (Cu) or are rather expensive (Au, Ag).

Even though the shape of the cross-section of the channel 3 is of no particular importance a circular shape is preferred. The diameter of the channel is preferably chosen to from about 0.1 mm to about 1.7 mm. A smaller diameter results in high risks of clogging when injecting crude samples; also it could generate a high back pressure in the system. Channel-diameters over 1.7 mm would not be suited for most analysis methods which employ flowing samples and use flow cells, such as, for example Flow Injection Analysis (FIA), because the flux in the channel could become non-laminar and the dispersion of the sample in the carrier could not be controlled any more.

As becomes apparent from FIG. 2 the channel 3 is directly etched or engraved or otherwise machined into the surface of the body such, that the channel is a spiralled groove, which extends generally planarly between the inlet opening 4 and the outlet opening 5 to the recess 6. The open top of the groove is covered by a heat conductive cover sheet 9, which is preferably made of the same material as the body 3. Throughholes 11 in the cover sheet 9 and threaded bores 10a–c (FIG. 1) allow to fix the cover sheet 9 to the body by means of screws. Of course the two parts could also be glued or bonded together, or simply be held together with tight clamps.

The channel 3 can be coated with a thin layer of a chemically inert material, such as, for example, gold, silica, Teflon®, metal oxides, and the like. The coating does not degrade the thermal equilibration even if coatings are chosen which have only a small or no thermal conductivity at all, because of the samll thickness of the layer, of, for example, only 1 μm.

In FIG. 2 it is also indicated that the flow cell 1 is preferably enclosed within an outer jacket 12, which is made of a non-heat conductive material, preferably of plexiglass. The plexiglass jacket 12 surrounds the flow-cell, which is preferably made of aluminium, and protects it against the environment and in particular against air currents, and helps thus to reduce the baseline noise and drifts of the detected signal. It is clear that openings are provided in the outer jacket 12, which conform to the inlet opening 4 of the channel 3 and to the exit opening 8 of the flow cell 1. Also there are provisions made for the attachment of the necessary electrical wiring or additional capillary tubings.

Figure 3:
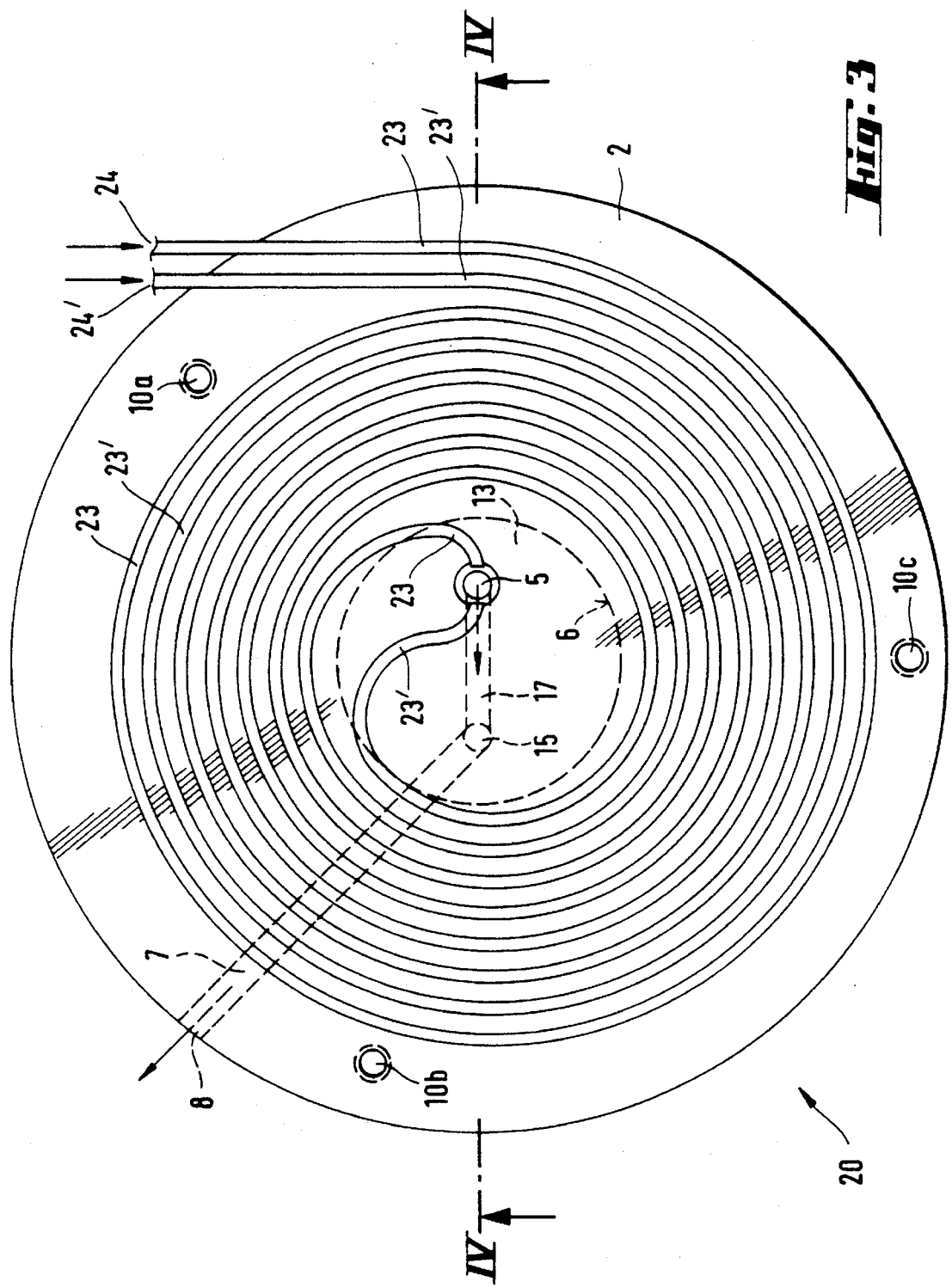
FIG. 3 is a top view of a second embodiment of the body of the flow cell, (without its outer jacket)
Figure 4:
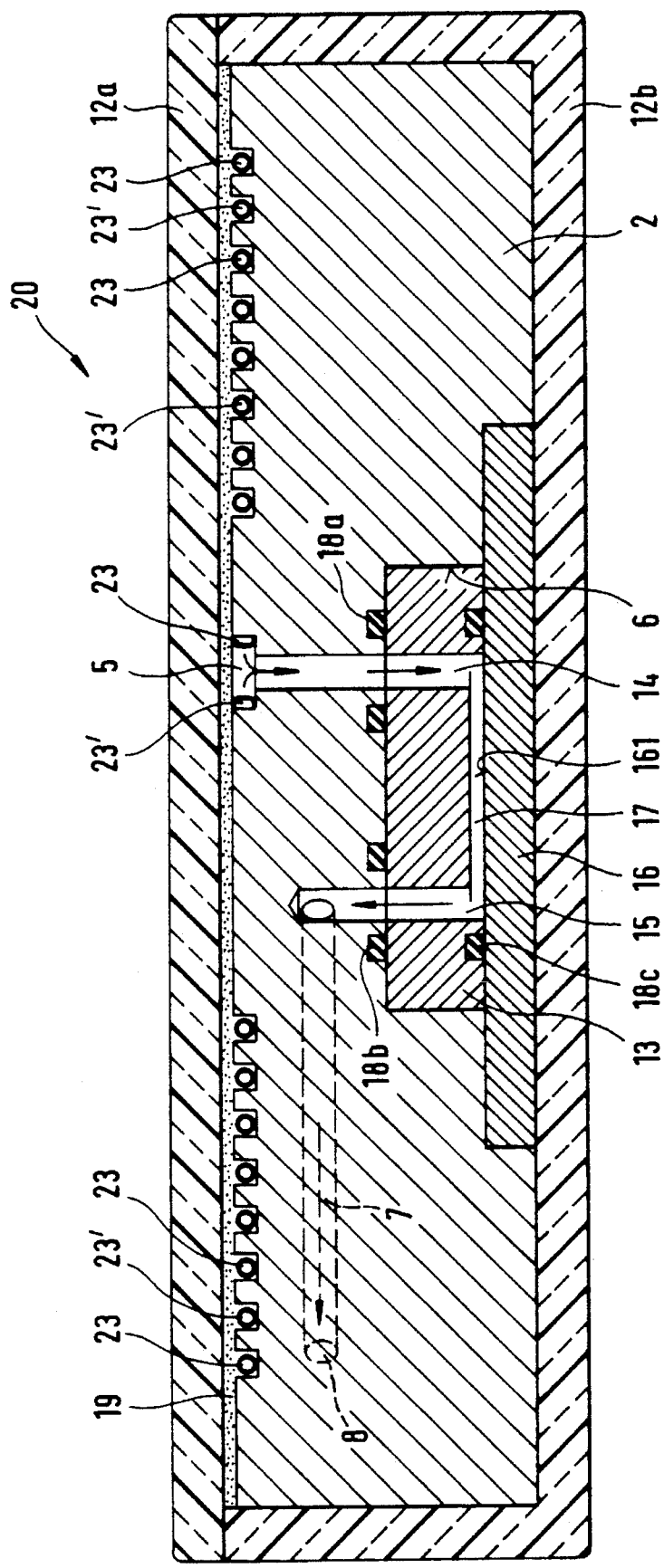
FIG. 4 is a sectioned view of the second embodiment of the flow cell as a whole along section line IV—IV in FIG. 3 (with outer jacket).

In FIGS. 3 and 4 a second embodiment 20 of the flow cell according to the invention is depicted. It differs from the first embodiment 1 insofar as its body 2 has two spirally shaped flow channels 23, 23', which have two separate inlet openings 24, 24'. The two channels end in one common outlet opening 5, which again is located about in the central part of the body 2, end extends about vertically through the body 2 and ends at the recess 6 below the spirally wound channels 23, 23'. This design of the flow cell 20 allows a simultaneous injection of two substances which are separately brought in front of the sensor in the measuring chamber, where they arc finally allowed to react, so that the heat of reaction can be immediatly measured without the need to cover the thermopile with an enzyme or another reactive substance. There could be provided more than two channels for further improving the flexibility of application of the device. However, it is to be noted, that further channels require additional space such, that the size of the flow cell grows, making it more difficult to achieve the desired low thermal mass.

In the depicted embodiment of the flow cell 20 the channels 23, 23' are not grooves which are directly formed into the surface of the body 2, but the channels 23, 23' are two stainless steel tubes which are embedded onto or preferably into the surface of the body 2.

As shown in FIG. 4 the body 2 of the second embodiment of the flow cell 20 can be enclosed within an outer jacket 12a, 12b of a non-heat conductive material, preferably plexiglass, in order to better protect it against influences of the surrounding environment. While in the embodiment according to FIG. 2 the plexiglass jacket is a kind of housing, in the embodiment according to FIG. 4 the outer jacket 12a, 12b is in intimate contact with the body 2 of the flow cell 20. In order to further improve thermal equilibration between the windings of the stell tubes 23, 23' a heat conductive paste 19 can be provided between the jacket part 12a which covers the tubes and the tubes.

As already indicated before, the thermoelectric detector, which is accommodated within the measuring chamber is preferably a thermopile. The advantage of using thermopiles as sensors, relies in the fact that thermopiles have a high common mode rejection ratio (CMRR). With thermopiles direct measurements of the temperature differences can be made, thus avoiding the need of controlling the temperature of the surrounding environment, even when temperature changes smaller than 1 mK are to be detected. However, in order to be able to detect such small temperature differences also in flowing, usually aqueous samples the temperature fluctuations of the flowing sample have to be considerably diminished. By using the flow sensor according to the invention in conjunction with a thermopile the temperature fluctuations of the flowing sample can be kept lower than than 0.05 mK at a frequency of 0.02 Hz. The flow cell according to the invention allows very quick exchanges of heat with its surroundings, as the sample is flowing through it. The temperature fluctuations of the sample are equilibrated solely in a passive way by circulating the sample within the heat conductive (metallic) body of the flow cell. In other words, the temperature of the sample is self-stabilized as it flows towards the measuring chamber with the thermopile (sensor), without any external thermostatization.

What is claimed is:
1. A flow cell for calorimetric measurements comprising a body with at least two flow channels sharing one common outlet opening, and each one of said at least two flow channels having a separate inlet opening and extending to said outlet opening, said flow cell further comprising a thermoelectric detector for monitoring temperature changes, which occur during chemical or biochemical processes in a measuring volume being located below said at least two flow channels in close vicinity to said outlet opening of said at least two flow channels wherein said outlet opening extends vertically through said body and ends in a recess, which is provided in said body of said flow cell below said at least two flow channels, said recess being adapted to accommodate said thermoelectric detector and a spacer element, which is arranged between said body and said thermoelectric detector, said spacer element being provided with central bores, which communicate with said outlet opening, with said measuring volume and with an exit channel, which is provided in said body, and said spacer element having a height such, that a gap between said spacer element and an active surface of said thermoelectric detector defines said measuring volume, and whereby said body of said flow cell has a good thermal conductivity such, that fluids flowing through said at least two flow channels are thermostatizised prior to entering said measuring volume solely by flowing through said at least two flow channels and free of any external thermostatization means.

2. A flow cell for calorimetric measurements comprising a body with at least one flow channel, which extends between an inlet opening and an outlet opening, and which is spiral shaped such, that a respective outer winding, thermally shields a respective neighboring inner winding said flow cell further comprising a thermoelectric detector for monitoring temperature changes, which occur during chemical or biochemical processes in a measuring volume being located below said at least one flow channel in close vicinity to said outlet opening of said at least one flow channel, wherein said outlet opening extends vertically through said body and ends in a recess, which is provided in said body of said flow cell below said at least one channel, said recess being adapted to accommodate said thermoelectric detector and a spacer element, which is arranged between said body and said thermoelectric detector, said spacer element being provided with central bores, which communicate with said outlet opening, with said measuring volume and with an exit channel, which is provided in said body, and said spacer element having a height such, that a gap between said spacer element and an active surface of said thermoelectric detector defines said measuring volume, and whereby said body of said flow cell has a good thermal conductivity such, that a fluid flowing through said flow channel is thermostatizised prior to entering said measuring volume solely by flowing through said flow channel and free of any external thermostatization means.

3. A flow cell for calorimetric measurements comprising a body with at least one flow channel, which flow channel extends between an inlet opening and an outlet opening, and a thermoelectric detector for monitoring temperature changes, which occur during chemical or biochemical processes in a measuring volume being located below said at least one flow channel in close vicinity to said outlet opening of said at least one flow channel, wherein said outlet opening extends vertically through said body and ends in a recess, which is provided in said body of said flow cell below said at least one channel, said recess being adapted to accommodate said thermoelectric detector and a spacer element, which is arranged between said body and said thermoelectric detector, said spacer element being provided with central bores, which communicate with said outlet opening, with said measuring volume and with an exit channel, which is provided in said body, and said spacer element having a height such, that a gap between said spacer element and an active surface of said thermoelectric detector defines said measuring volume, and whereby said body of said flow cell has a good thermal conductivity such, that a fluid flowing through said flow channel is thermostatizised prior to entering said measuring volume solely by flowing through said flow channel and free of any external thermostatization means.

4. A flow cell according to claim 3, wherein said thermal conductivity of said body is greater than about 0.8 W/cm.K.

5. A flow cell according to claim 3, wherein said body has a thermal mass, being the product of the specific heat capacity $C_p$ of the material of said body in J/g.K and of the mass in grams, of said material, that is less than 50 J/K.

6. A flow cell according to claim 3, wherein said flow channel has a length which results in a residence time of said fluid flowing through said flow channel prior to entering said measuring volume, which is greater than about 0.5 seconds.

7. A flow cell according to claim 3, wherein said flow channel extends about in a planar manner across said body and further wherein said inlet opening is located at the periphery of said body while said outlet opening is located about at a central part of said body.

8. A flow cell according to claim 7, wherein said flow channel has a curved shape, with a radius of curvature, that gradually decreases from said inlet opening to said outlet opening.

9. A flow cell according to claim 8, wherein said flow channel is spirally shaped such, that a respective outer winding thermally shields a respective neighbouring inner winding.

10. A flow cell according to claim 9, wherein said flow channel has an about circular cross section with a diameter which is between about 0.1mm to about 1.7 mm.

11. A flow cell according to claim 3, wherein said at least one flow channel is two flow channels each, sharing one common outlet opening, which communicates with said measuring volume, and each one of said flow channels includes a separate inlet opening.

12. A flow cell according to claim 3, wherein said recess is adapted to accomodate spacer elements of different heights, thus providing for an easy adjustment of the size of said measuring volume.

13. A flow cell according to claim 3, wherein said spacer element is made of a material which has a thermal conductivity, about equal to the thermal conductivity of said flow cell.

14. A flow cell according to claim 13 wherein said spacer element is made of the same materials as said body.

15. A flow cell according to claim 3, wherein said at least one channel is directly etched or engraved into said body and an open top of said at least one channel is covered by a heat conductive cover sheet.

16. A flow cell according to claim 15, wherein said body and said cover sheet are enclosed within an outer jacket, which is made of a non-heat conductive material.

17. A flow cell according to claim 16 wherein the outer jacket is made of plexiglass.

18. A flow cell according to claim 3, wherein said body is made of aluminium.

19. A flow cell according to claim 3, wherein said thermoelectric detector is a thermopile.

* * * * *